(12) United States Patent
Baril et al.

(10) Patent No.: US 10,729,424 B2
(45) Date of Patent: Aug. 4, 2020

(54) LOADING FIXTURE FOR USE WITH ENDOSCOPIC STITCHING DEVICE

(71) Applicant: Covidien LP, Mansfield, MA (US)

(72) Inventors: Jacob Baril, White Plains, NY (US); Jaroslaw Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 112 days.

(21) Appl. No.: 15/606,168

(22) Filed: May 26, 2017

(65) Prior Publication Data
US 2017/0360431 A1   Dec. 21, 2017

Related U.S. Application Data

(60) Provisional application No. 62/352,035, filed on Jun. 20, 2016.

(51) Int. Cl.
| | | |
|---|---|---|
| A61B 17/04 | (2006.01) | |
| A61B 17/06 | (2006.01) | |
| A61B 17/062 | (2006.01) | |
| A61B 17/00 | (2006.01) | |
| A61B 17/29 | (2006.01) | |

(52) U.S. Cl.
CPC ...... *A61B 17/0469* (2013.01); *A61B 17/0625* (2013.01); *A61B 17/06066* (2013.01); *A61B 17/06114* (2013.01); *A61B 17/0482* (2013.01); *A61B 2017/0053* (2013.01); *A61B 2017/06047* (2013.01); *A61B 2017/2926* (2013.01)

(58) Field of Classification Search
CPC ........ A61B 2017/0053; A61B 17/0469; A61B 2017/0609; A61B 2017/2926; A61B 17/00234

USPC .......................................................... 606/145
See application file for complete search history.

(56) References Cited

U.S. PATENT DOCUMENTS

| | | | | |
|---|---|---|---|---|
| 5,591,181 A | * | 1/1997 | Stone | A61B 17/0469 206/239 |
| 5,669,490 A | * | 9/1997 | Colligan | A61B 17/0469 206/227 |
| 6,126,666 A | * | 10/2000 | Trapp | A61B 17/0469 206/339 |
| 8,177,794 B2 | | 5/2012 | Cabrera et al. | |
| 8,226,667 B2 | | 7/2012 | Viola et al. | |
| 8,246,637 B2 | | 8/2012 | Viola et al. | |
| 8,292,905 B2 | | 10/2012 | Taylor et al. | |

(Continued)

OTHER PUBLICATIONS

Extended European Search Report issued in European Application No. 17176570.4 dated Dec. 18, 2017.

*Primary Examiner* — Christopher L Templeton
*Assistant Examiner* — Andrew P. Restaino
(74) *Attorney, Agent, or Firm* — Carter, DeLuca & Farrell LLP

(57) ABSTRACT

A loading fixture for use with an endoscopic stitching device includes a needle and a loading portion configured to receive jaws of the endoscopic stitching device. The loading portion includes a shuttle configured to detachably support the needle thereon. The shuttle is transversely slidable such that the needle supported on the shuttle engages at least one of the jaws of the endoscopic stitching device. The loading portion further includes guides to position the jaws of the endoscopic stitching device therebetween and a biasing member configured to bias the shuttle toward one of the guides.

21 Claims, 3 Drawing Sheets

(56) References Cited

U.S. PATENT DOCUMENTS

| | | |
|---|---|---|
| 8,292,906 B2 | 10/2012 | Taylor et al. |
| 8,337,515 B2 | 12/2012 | Viola et al. |
| 8,372,090 B2 | 2/2013 | Wingardner et al. |
| 8,454,631 B2 | 6/2013 | Viola et al. |
| 8,460,275 B2 | 6/2013 | Taylor et al. |
| 8,490,713 B2 | 7/2013 | Furnish et al. |
| 8,496,674 B2 | 7/2013 | Cabrera et al. |
| 8,506,581 B2 | 8/2013 | Wingardner, III et al. |
| 8,628,545 B2 | 1/2014 | Cabrera et al. |
| 8,636,752 B2 | 1/2014 | Cabrera et al. |
| 8,747,424 B2 | 6/2014 | Taylor et al. |
| D708,746 S | 7/2014 | Cabrera et al. |
| 8,864,776 B2 | 10/2014 | Bogart et al. |
| 8,968,340 B2 | 3/2015 | Chowaniec et al. |
| 8,968,342 B2 | 3/2015 | Wingardner, III et al. |
| 9,113,860 B2 | 8/2015 | Viola et al. |
| 9,125,644 B2 * | 9/2015 | Lane .................. A61B 17/0467 |
| 9,271,723 B2 | 3/2016 | Taylor et al. |
| 9,615,824 B2 | 4/2017 | Furnish et al. |
| 2009/0312773 A1 | 12/2009 | Cabrera et al. |
| 2010/0228270 A1 | 9/2010 | Bogart et al. |
| 2011/0040308 A1 | 2/2011 | Cabrera et al. |
| 2015/0351749 A1 * | 12/2015 | Martin ............... A61B 17/0469 606/145 |

* cited by examiner

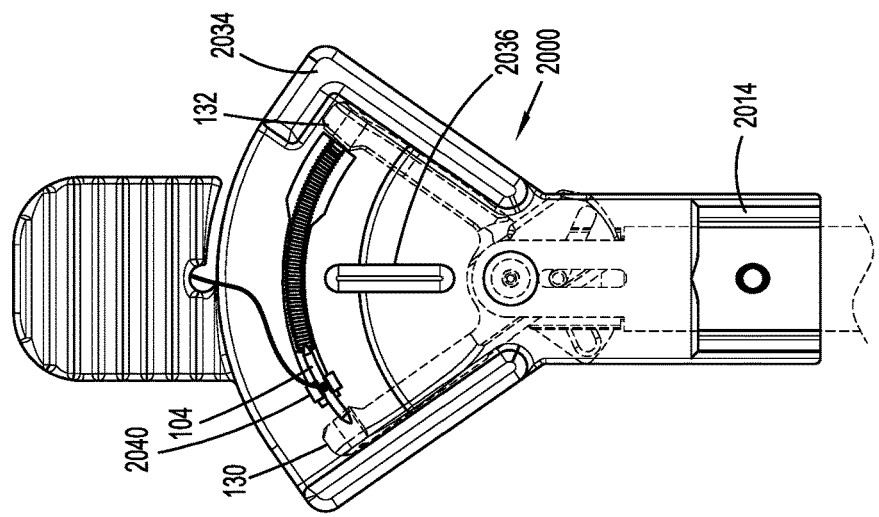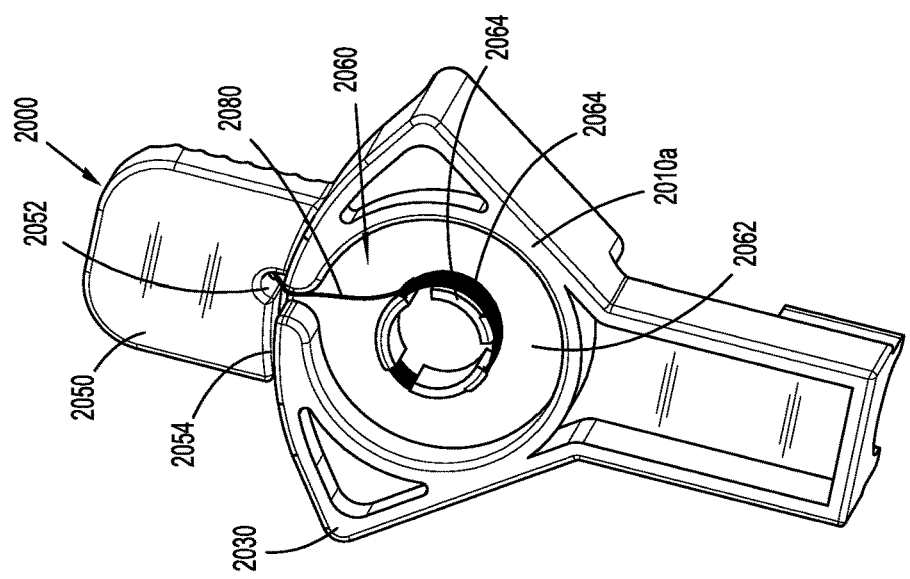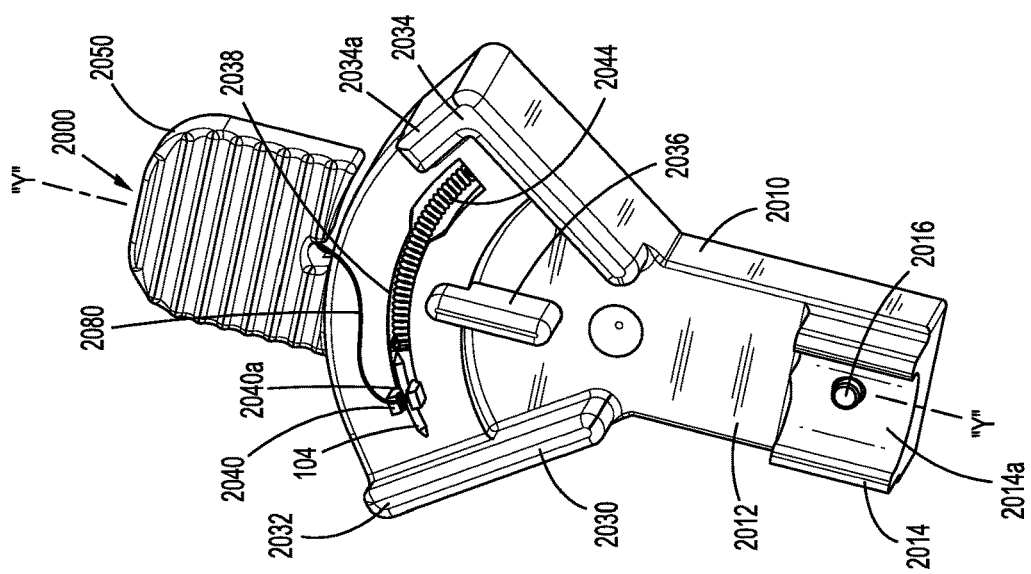

LOADING FIXTURE FOR USE WITH ENDOSCOPIC STITCHING DEVICE

CROSS-REFERENCE TO RELATED APPLICATIONS

This application claims the benefit of and priority to U.S. Provisional Patent Application No. 62/352,035 filed Jun. 20, 2016, the entire disclosure of which is incorporated by reference herein.

BACKGROUND

Technical Field

The present disclosure relates to devices for use with suturing or stitching and, more particularly, to a loading fixture for positioning a surgical needle on devices for endoscopic suturing and/or stitching through an access tube or the like.

Background

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. In such surgical procedures, it is necessary to manipulate a surgical needle, having a length of suture material attached thereto, with a surgical suturing device. Therefore, a need exists for simple and effective devices capable of precisely positioning a surgical needle for receipt by a surgical suturing device.

SUMMARY

The present disclosure describes a loading fixture that demonstrates a practical approach to meeting the performance requirements and overcoming usability challenges associated with precisely positioning a surgical needle for receipt by a surgical suturing device. In accordance with an embodiment of the present disclosure, there is provided a loading fixture for use with an endoscopic stitching device. The loading fixture includes a needle and a loading portion configured to receive jaws of the endoscopic stitching device. The loading portion includes a shuttle, guides, and a biasing member. The shuttle is configured to detachably support the needle thereon. The shuttle is transversely slidable such that the needle supported on the shuttle engages at least one of the jaws of the endoscopic stitching device. The guides are configured to position the jaws of the endoscopic stitching device therebetween. The biasing member is configured to bias the shuttle toward one of the guides.

In an embodiment, the loading portion may define a slot configured to slidably receive the shuttle. The slot of the loading portion may define an arc.

In another embodiment, the guides may be disposed on opposing peripheral sides of the loading portion. One of the guides may be L-shaped.

In yet another embodiment, the loading fixture may further include a neck portion configured to securely engage a support member of a tool assembly of the endoscopic stitching device. The neck portion may include a support including a U-shaped cross-section configured to receive the support member of the tool assembly.

In still another embodiment, the loading portion may define a spooling portion configured to retain a suture thereon. The spooling portion may be disposed on a first surface of the loading portion and the shuttle may be disposed on a second surface of the loading portion, wherein the first surface is opposite of the second surface.

In still yet another embodiment, the loading fixture may further include a grip portion extending distally from the loading portion. The grip portion and the loading portion may define a slot configured to receive the suture therethrough.

In accordance with another embodiment of the present disclosure, there is provided an endoscopic stitching device assembly. The endoscopic stitching device assembly includes a tool assembly and a loading fixture. The tool assembly includes a support member, first and second jaws operatively coupled with the support member, and first and second needle receiving blades slidably disposed in the respective first and second jaws. The first and second jaws are configured to pivot between open and closed positions.

In accordance with this embodiment, the loading fixture is configured to be detachably secured with the tool assembly. The loading fixture includes a needle and a loading portion configured to receive the first and second jaws of the tool assembly. The loading portion includes a shuttle configured to detachably support the needle thereon, guides to position the first and second jaws of the tool assembly therebetween, and a biasing member configured to bias the shuttle toward one of the guides. The shuttle is transversely slidable such that the needle supported on the shuttle engages at least one of the first or second needle receiving blades of the tool assembly.

In an embodiment, the loading portion may further include a central guide portion configured to limit distal displacement of the first and second jaws in the closed position.

DETAILED DESCRIPTION OF THE DRAWINGS

The foregoing objects, features and advantages of the disclosure will become more apparent from a reading of the following description in connection with the accompanying drawings, in which:

FIG. 3 is a top perspective view of the loading fixture in accordance with an embodiment of the present disclosure;

FIG. 4 is a bottom perspective view of the loading fixture of FIG. 3; and

FIG. 5 is a top view of the loading fixture of FIG. 3, illustrating use with a tool assembly of the stitching device of FIG. 1 shown in phantom.

DETAILED DESCRIPTION

Figure 1:
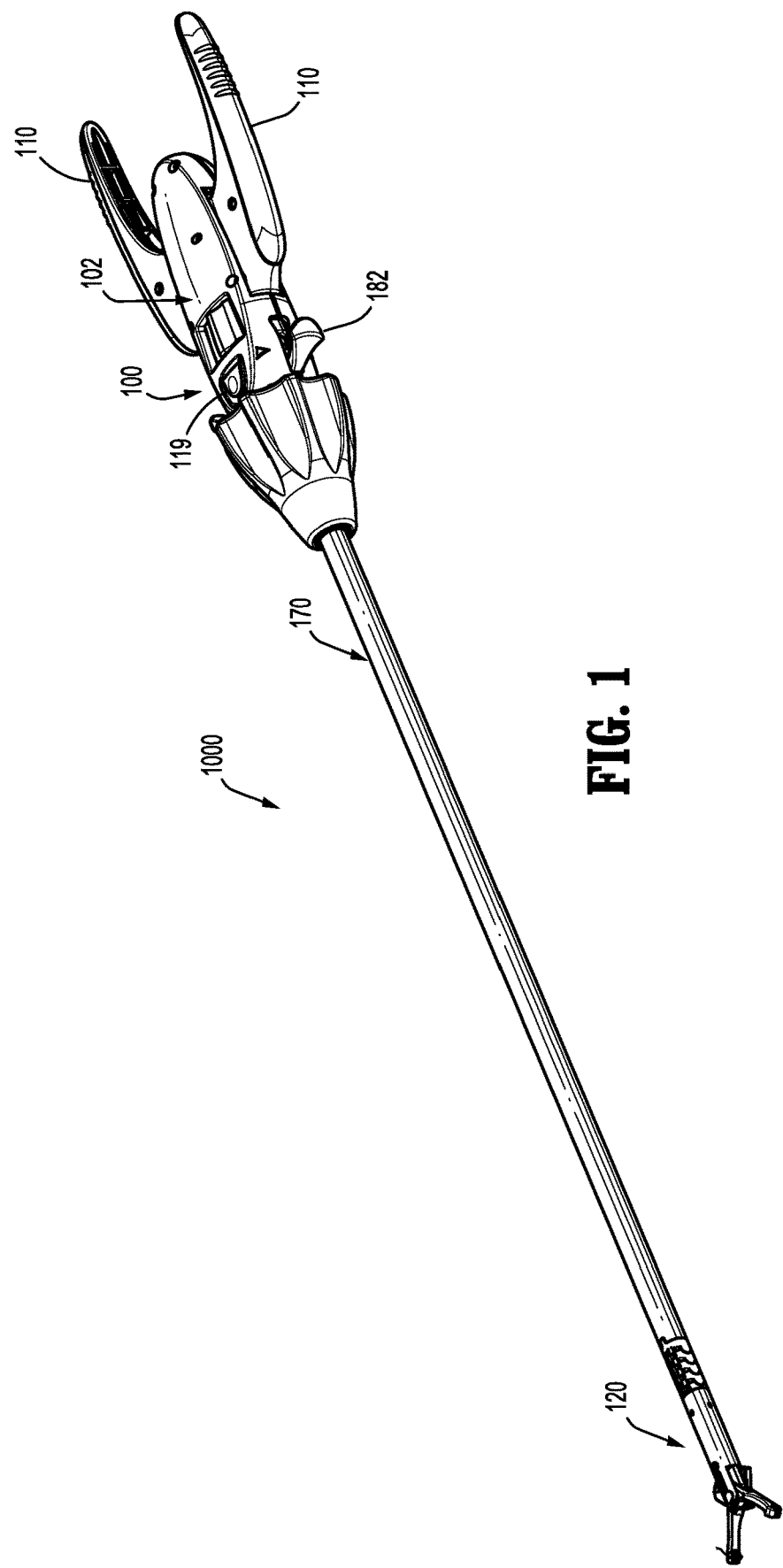
FIG. 1 is a perspective view of a stitching device for use with a loading fixture in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, an embodiment of the present disclosure is generally shown as a stitching device 1000. Stitching device 1000 is adapted to be particularly useful in endoscopic or laparoscopic procedures, wherein an endoscopic portion of stitching device 1000 such as, e.g., a tool assembly 120, is insertable into an operative site, via a cannula assembly or the like (not shown). Stitching device 1000 includes a handle assembly 100, an elongate shaft assembly 170 extending distally from handle assembly 100, and tool assembly 120 detachably supported on a distal end of elongate shaft assembly 170. Such a configuration facilitates, e.g., sterilization of stitching device 1000 and loading of needle on tool assembly 120.

Figure 2:
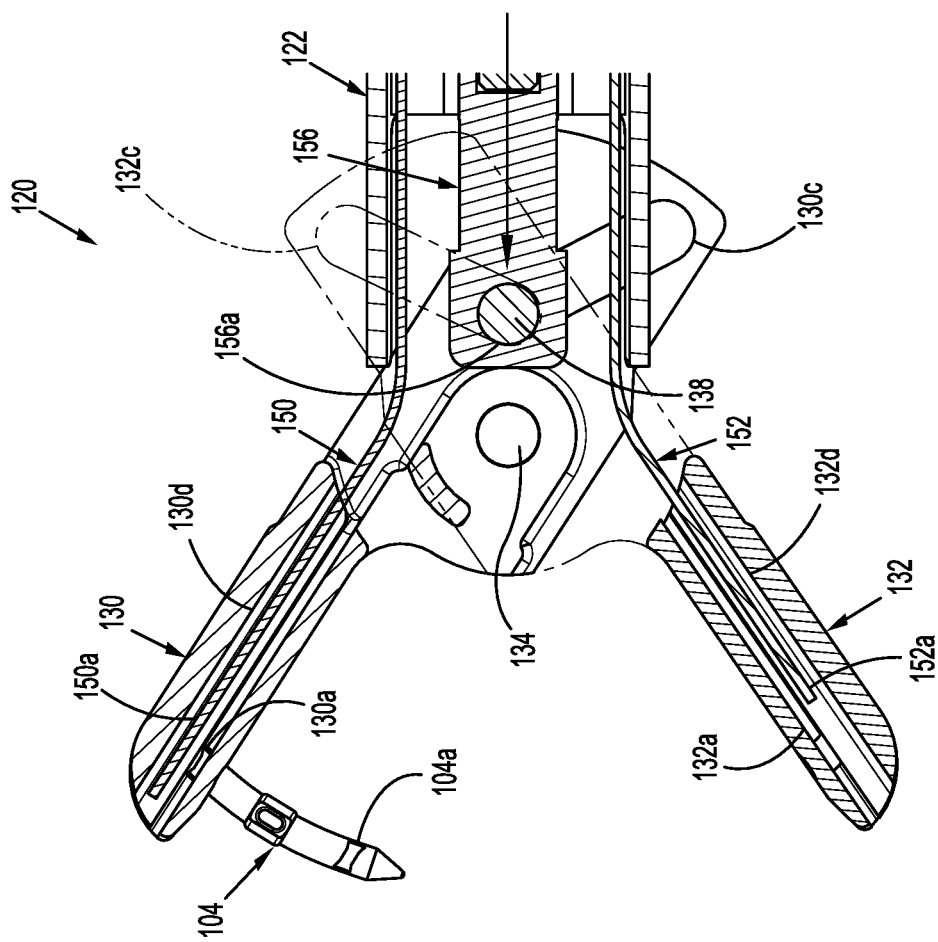
FIG. 2 is a partial cross-sectional view of a tool assembly of the stitching device of FIG. 1.

With reference to FIGS. 1 and 2, tool assembly 120 includes a support member 122 and jaws 130, 132 pivotably mounted on support member 122 by means of a jaw pivot pin 134. To move jaws 130, 132 between an open position and a closed position, an axial rod 156 has a camming pin 138 mounted at a distal end 156a thereof. Camming pin 138 rides in angled camming slots 130c, 132c defined in respective jaws 130, 132 such that axial or longitudinal movement of axial rod 156 causes jaws 130, 132 to be cammed between the open and closed positions.

Tool assembly 120 further includes a pair of needle engaging members or blades 150, 152 which are slidably supported within support member 122. Each blade 150, 152 includes a distal end 150a, 152a slidably extending into blade receiving channels 130d, 132d of respective jaws 130, 132. Channels 130d, 132d are dimensioned to at least partially intersect respective needle recesses 130a, 132a. Thus, by advancing blade 150 or 152 within respective channel 130d, 132d, distal end 150a, 152a of advancing blade 150, 152 engages or "locks in" a groove 104a formed in needle 104 when at least a portion of needle 104 is received within respective needle recesses 130a, 132a.

With brief reference to FIG. 4, a suture 2080 is connected to needle 104. Suture 2080 may include a plurality of barbs oriented to resist movement in a direction opposite to the direction of travel.

With continued reference to FIGS. 1 and 2, handle assembly 100 includes a pair of handles 110 pivotably secured to housing 102. Handles 110 are operatively coupled to axial rod 156 such that when handles 110 are squeezed, axial rod 156 is displaced proximally. Axial rod 156 may be provided with, e.g., a biasing member (not shown), in the form of a return spring, to bias axial rod 156 to an initial position. Axial rod 156 is operatively coupled to jaws 130, 132 of tool assembly 120, such that axial displacement of axial rod 156 transitions jaws 130, 132 between the open and closed positions.

With particular reference to FIG. 1, handle assembly 100 further includes a lever 182 pivotably supported in housing 102 and extending transversely from housing 102. Lever 182 is operatively coupled to blades 150, 152 (FIG. 2) of tool assembly 120. Lever 182 may be pivoted to cause reciprocating axial displacement of blades 150, 152 to enable swapping of needle 104 between jaws 130, 132.

With continued reference to FIG. 1, handle assembly 100 further includes a slider 119 (FIG. 1) operatively coupled with lever 182 to slide lever 182 distally to transition handle assembly 100 to a reload mode. In the reload mode, both blades 150, 152 (FIG. 2) are in a distal-most position. In this manner, notches (not shown) formed in respective blades 150, 152 are aligned with or in registration with respective needle recesses 130a, 132a defined in respective jaws 130, 132. With the notches of blades 150, 152 aligned with or in registration with the respective needle recesses 130a, 132a of respective jaws 130, 132, needle 104 (FIG. 2) may be positioned or loaded into a selected one needle recess 130a, 132a of jaws 130, 132. Reference may be made to U.S. Pat. No. 8,628,545, entitled "Endoscopic Stitching Devices," the entire content of which is incorporated herein by reference, for a detailed discussed of the construction and operation of a handle assembly and a tool assembly.

With reference now to FIGS. 3 and 4, there is provided a loading fixture 2000 in accordance with an embodiment of the present disclosure. Loading fixture 2000 is configured to secure tool assembly 120 thereon to facilitate loading of needle 104 on jaws 130, 132. Loading fixture 2000 defines a longitudinal axis "Y-Y" and includes a body portion 2010 and a grip portion 2050. Grip portion 2050 may be textured, e.g., ridges, to improve gripping thereof by a user. Body portion 2010 and grip portion 2050 may be integrally formed as a single construct. Body portion 2010 includes a neck portion 2012 and a loading portion 2030. Neck portion 2012 is configured to secure support member 122 (FIG. 2) of tool assembly 120 thereon.

With particular reference to FIG. 3, neck portion 2012 includes a support 2014 including a U-shaped arcuate portion 2014a configured to receive and align support member 122 of tool assembly 120 thereon. Support 2014 may include a boss 2016 configured to be received in a bore (not shown) defined in support member 122 to further facilitate alignment of support member 122 of tool assembly 120 with support 2014.

Loading portion 2030 extends distally outward from neck portion 2012. Loading portion 2030 includes peripheral guides 2032, 2034 configured to position jaws 130, 132 of tool assembly 120 therebetween. Loading portion 2030 further includes a central guide 2036 positioned to be interposed between jaws 130, 132 of tool assembly 120 to limit distal displacement of jaws 130, 132 when jaws 130, 132 are in the closed position. In addition, at least one of peripheral guides 2032, 2034 may include a distal portion 2034a to limit distal displacement of jaws 130, 132 of tool assembly 120 when jaws 130, 132 are in the open position.

Loading portion 2030 further defines a slot 2038 defining an arc between peripheral guides 2032, 2034. Slot 2038 is configured to slidably receive a shuttle 2040 therein. Shuttle 2040 defines a slit 2040a configured to support needle 104. Loading portion 2030 further includes a biasing member 2044 within slot 2038 thereof to bias shuttle 2040 toward one of peripheral guides 2032, 2034.

Grip portion 2050 extends distally from loading portion 2030 of body portion 2010. Grip portion 2050 defines a bore 2052 extending therethrough and a slot 2054 in communication with bore 2052. Bore 2052 and slot 2054 are configured to receive suture 2080 connected to needle 104.

As illustrated in FIG. 4, on an opposing side 2010a of body portion 2010, body portion 2010 includes a spooling portion 2060. Spooling portion 2060 defines a recess 2062 and includes a winding portion 2064 to wind suture 2080 thereon.

With reference now to FIG. 5, in use, stitching device 1000 is first transitioned to the reload mode by sliding slider 119 (FIG. 1) distally such that both blades 150, 152 (FIG. 2) are in the distal-most position. In this manner, notches (not shown) formed in respective blades 150, 152 are aligned with or in registration with respective needle recesses 130a, 132a defined in respective jaws 130, 132. With the notches of blades 150, 152 aligned with or in registration with the respective needle recesses 130a, 132a of respective jaws 130, 132, needle 104 (FIG. 2) may be positioned or loaded into a selected one needle recess 130a, 132a of jaws 130, 132.

At this time, support member 122 of tool assembly 120 is aligned with body portion 2010 of loading fixture 2000 and received in support 2014 such that boss 2016 of support 2014 is received in the bore (not shown) defined in support member 122 of tool assembly 120. In this manner, jaw 132 engages peripheral guide 2034 and needle recess 130a of jaw 130 is aligned with needle 104 disposed on shuttle 2040. At this time, handles 110 (FIG. 1) may be squeezed to close jaws 130, 132. Once needle 104 is loaded or at least partially inserted into needle recesses 130a, 132a of jaws 130, 132, the notches (notches) of blades 150, 152 are in registration with respective grooves 104a of needle 104. With needle 104 positioned such that the notches of blades 150, 152 are in registration with needle recesses 130a, 130b, lever 182 is actuated or rotated so that only one blade 150, 152 is moved into engagement with needle 104 (FIG. 2) to hold needle 104, and the other blade 150, 152 is disengaged from needle 104. With only one blade 150, 152 engaged with needle 104, handles 110 may be released, thereby moving axial rod 156 distally to open jaws 130, 132.

With jaws 130, 132 in the open position and needle 104 loaded and held in jaw 130 or 132, jaws 130, 132 may be positioned about or over a target tissue and handles 110 may be actuated to approximate jaws 130, 132. As jaws 130, 132 are approximated, the exposed end of needle 104 is penetrated through the target tissue and enters opposed jaw 130 or 132. With needle 104 in opposed jaw 130 or 132, lever 182 is once again actuated or rotated so that blades 150, 152 are reversed. In so doing, needle 104 is swapped from one blade 150 or 152 to the other blade 150 or 152, and thus, loaded or held in the other jaw 130 or 132.

With needle 104 being swapped from one blade 150, 152 to another blade 150, 152, handles 110 may be released to thereby open jaws 130, 132 and draw needle 104 through the target tissue. In so doing, suture 2080 is also drawn through the tissue. The process is repeated, passing needle 104 between jaws 130, 132 and drawing suture 2080 through the target tissue, thereby suturing the target tissue as needed or desired.

Although the illustrative embodiments of the present disclosure have been described herein with reference to the accompanying drawings, the above description, disclosure, and figures should not be construed as limiting, but merely as exemplifications of particular embodiments. For example, spooling portion 2060 may be disposed on the same surface as shuttle 2040. Alternatively, spooling portion 2060 may be disposed on grip portion 2050. It is to be understood, therefore, that the disclosure is not limited to those precise embodiments, and that various other changes and modifications may be effected therein by one skilled in the art without departing from the scope or spirit of the disclosure.

What is claimed is:

1. A loading fixture for use with an endoscopic stitching device, comprising:
   a needle; and
   a loading portion configured to receive jaws of the endoscopic stitching device, the loading portion including:
   a shuttle configured to detachably support the needle thereon, the shuttle transversely slidable along a path such that the needle supported on the shuttle engages at least one of the jaws of the endoscopic stitching device;
   guides to position both jaws of the endoscopic stitching device therebetween; and
   a biasing member configured to bias the shuttle toward one of the guides, wherein the loading portion defines a slot configured to slidably receive at least a portion of the shuttle and receive the biasing member movably extending along the slot, the path of the shuttle being in registration with the slot.

2. The loading fixture according to claim 1, wherein the slot of the loading portion defines an arc.

3. The loading fixture according to claim 1, wherein the guides are disposed on opposing peripheral sides of the loading portion.

4. The loading fixture according to claim 1, wherein one of the guides is L-shaped.

5. The loading fixture according to claim 1, wherein the loading fixture further includes a neck portion configured to securely engage a support member of a tool assembly of the endoscopic stitching device.

6. The loading fixture according to claim 5, wherein the neck portion includes a support including a U-shaped cross-section configured to receive the support member of the tool assembly.

7. The loading fixture according to claim 1, wherein the loading portion defines a spooling portion configured to retain a suture thereon.

8. The loading fixture according to claim 7, wherein the spooling portion is disposed on a first surface of the loading portion and the shuttle is disposed on a second surface of the loading portion, the first surface opposite of the second surface.

9. The loading fixture according to claim 8, further comprising a grip portion extending distally from the loading portion.

10. The loading fixture according to claim 9, wherein the grip portion and the loading portion define a second slot configured to receive the suture therethrough.

11. The loading fixture according to claim 1, wherein the entire shuttle is movable with the needle supported thereon.

12. An endoscopic stitching device assembly, comprising:
    a tool assembly including:
    a support member;
    first and second jaws operatively coupled with the support member, the first and second jaws configured to pivot between open and closed positions; and
    first and second needle receiving blades slidably disposed in the respective first and second jaws; and
    a loading fixture configured to be detachably secured with the tool assembly, the loading fixture including:
    a needle; and a loading portion configured to receive the first and second jaws of the tool assembly, the loading portion including:
  a shuttle configured to detachably support the needle thereon, the shuttle transversely slidable such that the needle supported on the shuttle engages at least one of the first or second needle receiving blades of the tool assembly;
  guides to position the first and second jaws of the tool assembly therebetween; and
  a biasing member configured to bias the shuttle toward one of the guides, wherein the biasing member is aligned with a path of the shuttle.

13. The endoscopic stitching device assembly according to claim 12, wherein the loading portion defines a slot configured to slidably receive the shuttle.

14. The endoscopic stitching device assembly according to claim 13, wherein the slot of the loading portion defines an arc.

15. The endoscopic stitching device assembly according to claim 12, wherein the guides are disposed on opposing peripheral sides of the loading portion.

16. The endoscopic stitching device assembly according to claim 12, wherein the loading fixture further includes a neck portion configured to securely engage the support member of the tool assembly, the loading portion extending distally outward from the neck portion.

17. The endoscopic stitching device assembly according to claim 16, wherein the neck portion includes a support including a U-shaped cross-section configured to receive the support member of the tool assembly.

18. The endoscopic stitching device assembly accordingly to claim 12, wherein the loading portion defines a spooling portion configured to retain a suture thereon.

19. The endoscopic stitching device assembly according to claim 18, wherein the spooling portion is disposed on a first surface of the loading portion and the shuttle is disposed on a second surface of the loading portion, the first surface opposite of the second surface.

20. The endoscopic stitching device assembly according to claim 12, wherein the loading portion further includes a central guide portion configured to limit distal displacement of the first and second jaws in the closed position.

21. A loading fixture for use with an endoscopic stitching device comprising:
  a needle; and
  a loading portion configured to receive jaws of the endoscopic stitching device, the loading portion defining a slot, the loading portion including:
    a shuttle configured to detachably support the needle thereon, the shuttle slidable along a path such that the needle supported on the shuttle engages at least one of the jaws of the endoscopic stitching device;
    guides to position both jaws of the endoscopic stitching device therebetween; and
    a biasing member configured to bias the shuttle toward one of the guides, wherein the biasing member is disposed in the slot and transversely slidable therein such that the shuttle is movable in registration with the slot.

* * * * *